(12) United States Patent
Helentjaris et al.

(10) Patent No.: US 6,207,367 B1
(45) Date of Patent: Mar. 27, 2001

(54) PROCESS FOR GENETIC MAPPING FOR PLANT IDENTIFICATION AND BREEDING PURPOSES

(75) Inventors: Timothy George Helentjaris, Salt Lake County; Gretchen Jane King, Summit County, both of UT (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 07/525,312

(22) Filed: May 18, 1990

Related U.S. Application Data

(63) Continuation of application No. 07/143,298, filed on Jan. 7, 1988, now abandoned, which is a continuation of application No. 06/938,378, filed on Dec. 9, 1986, now abandoned, which is a continuation of application No. 06/498,464, filed on May 26, 1983, now abandoned.

(51) Int. Cl.[7] ..................................................... C12Q 1/68
(52) U.S. Cl. ................................................ 435/6; 47/DIG. 1
(58) Field of Search .......................... 47/DIG. 1; 536/27, 536/24.3; 435/6, 91, 172.3, 320.34, 320.1; 935/78; 436/63, 94, 504

(56) References Cited

U.S. PATENT DOCUMENTS

| | | | |
|---|---|---|---|
| 4,237,224 | 12/1980 | Cohen et al. | 435/68 |
| 4,259,444 | 3/1981 | Chakrabarty | 435/172 |
| 4,396,713 | * 8/1983 | Simpson et al. | 435/6 |

OTHER PUBLICATIONS

Burr et al, Genetics 98: 143 (1981).*
Helentjaris et al. (Helentjaris), "Construction of genetic linkage maps in maize and tomato using restriction fragment length polymorphisms," *Theor. App. Genet.*, vol. 72, pp. 761–769 (1986).*
Laboratory Manual—"Molecular Cloning", T. Maniatis, E.F. Fritsch, J. Sambrook Cold Spring Harbor Laboratory, (1982) pp. 11–15, 86–94, 150–161, 382–389.
"A Protocol for High Density Plasmid Screening", D. Hanahan, M. Meselson, Harvard University, Sep., 1978.
"Cloning of Double–Stranded cDNA", A. Estratiadis, L. Villa–Komaroff, *Genetic Engineering, Principles and Methods*, vol. 1 pp. 15–36, Plenum Press, New York (1979).
"Genetic Identification of Lines and Crosses Using Isoenzyme Electrophoresis", M.M. Goodman, C.W. Stuber 35th Annual Corn & Sorghum Research Conference, pp. 10–31.
"Utility of Ethidium Bromide in the Extraction from Whole Plants of High Modular Weight Maize DNA", N. Kisley, I. Rubenstein, Plant Physiol. vol. 66 1980 pp. 1140–1143.
"Construction of a Genetic Linkage Map in Man Using Restriction Fragment Length Polymorphisms", D. Botstein, R. White, M. Skolnick, R. Davis Submitted to The American Journal of Human Genetics, Nov. 15, 1979 Revised: Jan. 2, 1980 To appear May, 1980.

"The Application of Restriction Fragment Length Polymorphism to Plant Breeding", B. Burr, S.V. Evola, F.A. Burr, J.S. Beckman Genetic Engineering, Principles and Methods, vol. 5 pp. 45–59.
"Restriction fragment length polymorphisms in genetic improvement: methodologies, mapping and costs", J.S. Beckmann and M. Soller Theor Appl Genet (1983) 67:35–43.
"Genetic polymorphism in varietal identification and genetic improvement", M. Soller, J.S. Beckmann, Theor Appl Genet (1983) 67:25–33.
"Evaluation of Genomic Variability at the Nucleic Acid Level", C. Rivin, E. Zimmer, C. Cullis, V. Walbot, T. Huynh, R. Davis Plant Molecular Biology Reporter vol. 1:1 (1983) pp. 9–16.
"Molecular Markers in Plant Breeding", S. Tanksley Plant Molecular Biology Reporter vol. 1:1 (1983) pp. 3–8.
"Evaluation of Random cDNA Clones as Probes for Human Restriction Fragment Polymorphisms", T. Helentjaris, R. Gesteland Journal of Molecular and Applied Genetics 2:237–247 (1983).
"DNA Sequence Variants in th Gγ, Aγ, δ–and β–Gobin Gnes of Man", A. Jeffreys, Cell, vol. 18, 1–10, Sep. 1979.
"Polymorphic DNA region adjacent to the 5' end of the human insulin gene", G. Bell, J. Karam, W. Rutter, Proc. Natl. Acad. Sci. USA vol. 78 No. 9 Sep./1981 pp. 5759–5763.
"Prenatal diagnosis of sickle cell anemia by restriction endonuclease analysis: HindIII polymorphisms in γ–golibin genes extend test applicability", J. Phillips III, S. Panny, H. Kazazian, Jr., C. Boehm, A. Scott, K. Smith Proc. Natl. Acad. Sci. USA vol. 77, No. 5, pp. 2853–2856, May 1980 Genetics.
"Construction of Genetic Linkage Map in Man Using Restriction Fragment Length Polymorphisms", D. Botstein, R. White, M. Skolnick, R. Davis Am J Hum Genet 32:314–331, 1980.
"An Electron Microscope Study of the DNA Sequence Organization of the Human Genome", P. Deininger, C. Schmid J. Mol. Biol. (1976), 106, 773–790.
"The isolation of cloned cDNA sequences which are differentially expressed in human lymphocytes and fibroblasts", J. Crampton, S. Humphries, D. Woods, R. Williamson, vol. 8 No. 24, 6007 1980 Nucleic Acids Research, Received Nov. 3, 1980.

(List continued on next page.)

Primary Examiner—James Martinell
(74) Attorney, Agent, or Firm—Foley & Lardner

(57) ABSTRACT

The invention is in a process of genetic mapping for plant identification and breeding purposes. The process utilizes restriction fragment technology and detection of polymorphisms to build up a genomic "fingerprint" for a variety or isolate. The "fingerprint" is then compared to "fingerprints" of other varieties or isolates to determine both the degree of relatedness and homozygosity for identification and breeding purposes.

5 Claims, 5 Drawing Sheets

OTHER PUBLICATIONS

"The Expression of Three Abundance Classes of Messenger RNA in Mouse Tissues", N. Hastie, J. Bishop Cell, vol. 9, 761–774, Dec. 1976 (Part 2).

"The Ovalbumin Gene: Alleles Created by Mutations in the Intervening Sequences of the Natural Gene", E. Lai, S. Woo, A. Dugaiczyk, B. O'Malley Cell, vol. 16, 201–211, Jan. 1979.

"A Rapid Boiling Method for the Preparation of Bacterial Plasmids", D. Holmes, M. Quigley; Analytical Biochemistry 114, 193–197 (1981).

"A rapid alkaline extraction procedure for screening recombinant plasmid DNA", H.C. Birnboim, J. Doly, vol. 7 No. 6, 1513, 1979 Nucleic Acids Research.

"The Chromosome of Bacteriophage T5", G.S. Hayward, M.G. Smith J. Mol. Biol. (1972) 63, 383–395.

"Efficient transfer of large DNA Fragments from agarose gels to diazobenzyloxy–methyl–paper and rapid hybridization by using dextran sulfate", G. Wahl, M. Stern, G. Stark, Proc. Natl. Acad. Sci. USA vol. 76, No. 8 pp. 3683–3687 Aug./1979.

"Efficient Transcription of RNA into DNA by Avian Sarcoma Virus Polymerase", J. Taylor, R. Illmensee, J. Summers Biochimica et Biophysica Acta, 442 (1976) 324–330.

"Evolutionary tree for apes and humans based on cleavage maps of mitochondrial DNA", S.D. Ferris, A.C. Wilson, W.M. Brown, vol. 78, No. 4, pp. 2432–2436, Apr. 1981 Evolution.

"Sequence and organization of the human mitochondrial genome", S. Anderson, A.T. Bankier, B.G. Barrell, M.H.L. de Bruijn, A.R. Coulson, J. Drouin', I.C. Eperon, D.P. Nierlich', B. A. Roe, F. Sanger, P. H. Schreier', A.J.H. Smith R. Staden, I.G. Young, Nature vol. 290 Apr. 9, 1981, p. 457.

Lewin; Science 244: 1033 (1989).*

"Restriction Fragment Length Polymorphisms and Genetic Improvement" by Soller et al., (Published Presentation) Oct. 4–8, 1982: pp. 396–404.

Flavell et al: Cold Spring Harbor Symp. Quant. Biol. 45, Pt. 2, 501 (1981).*

Wyman et al: Proc. Natl. Acad. Sci. USA, 77, 6754 (1980).*

Little et al: Nature 285, 144 (1980).*

Bishop et al: in *Banbury Report 4: Cancer Incidence in Defined Populations*, Cold Spring Harbor, 1980, pp. 421–433.*

Mendel, "Experiments in plant hybridization", Verb. naturf. Ver. xx.iv. (1866) Translation published in *Genetics*, W.H. Freeman & Co., San Francisco, 1981, pp. 8–17.*

Beckman; Meeting at the Weizzmann Institute in Israel. Bat–Sheva Seminar on Nitrogen Fixation, Sep. 1–9, 1981.*

Rom; Development of Restriction Fragment Length Polymorphism Techniques in Plants as a Tool for Strain Identification and Breeding, Abstract, Masters Thesis, Hebrew University of Jerusalem (1982).*

Burr et al; in Genetic Engineering: Principles and Methods, vol. 8, 1983, Setlow et al (ed.), Plenum Pub. Corp., pp. 45–59.*

Phillips et al; Implications of Molecular Geneticx Theory to Corn Breeding, 1983, presentation to the nineteenth Illinois Corn Breeders School, pp. 14, 15, and 17–28.*

* cited by examiner

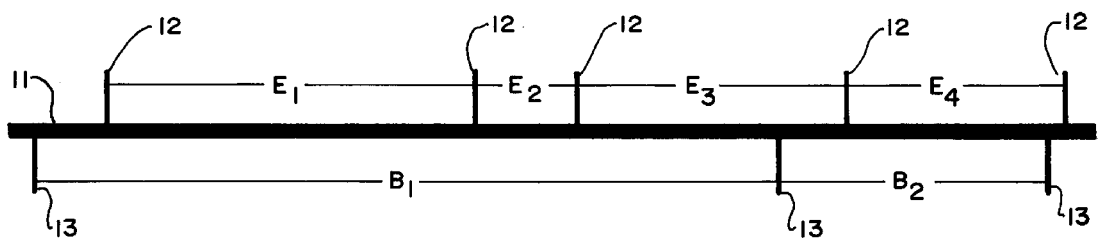
FIG. 2
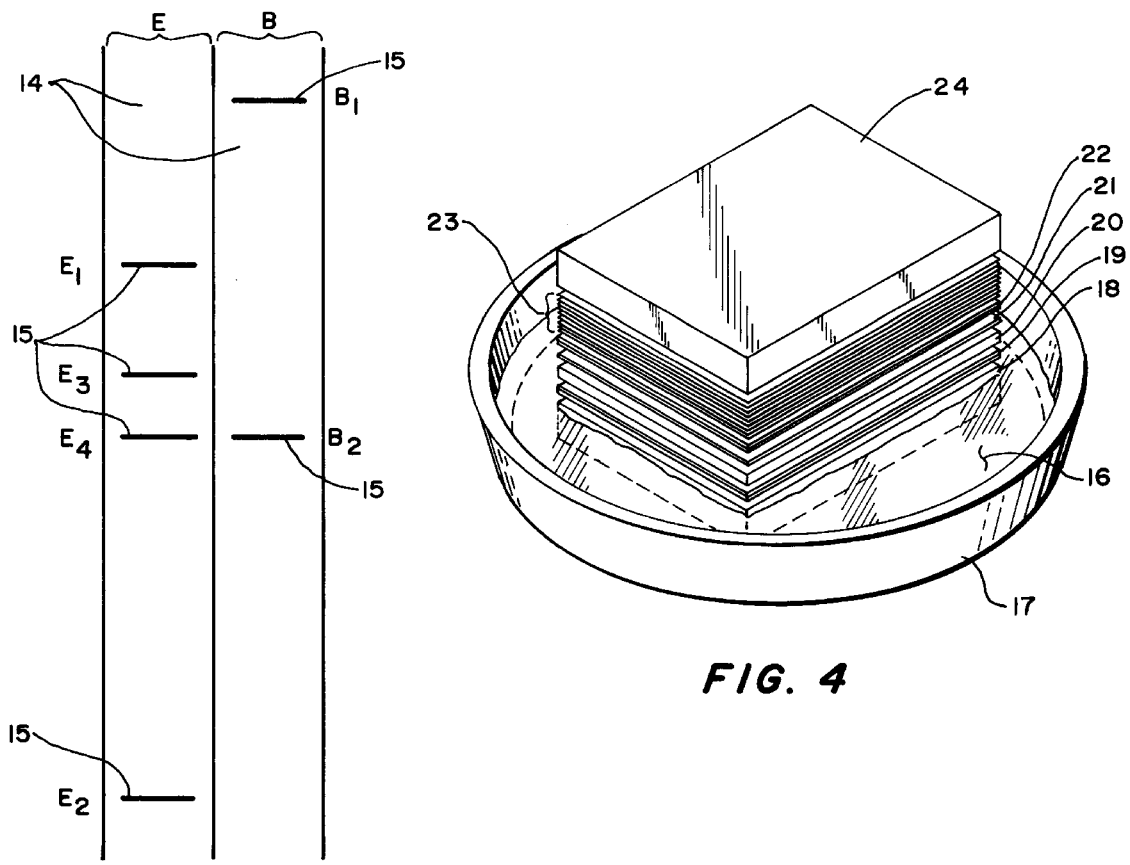
FIG. 3
FIG. 4

FIG. 7

PROCESS FOR GENETIC MAPPING FOR PLANT IDENTIFICATION AND BREEDING PURPOSES

This application is a continuation application of Ser. No. 07/143,298 filed Jan. 7, 1988, now abandoned, which is a continuation application of Ser. No. 06/938,378 filed Dec. 9, 1986, now abandoned, which is a continuation application of Ser. No. 06/498,464 filed May 26, 1983, now abandoned.

BACKGROUND OF THE INVENTION

1. Field

The invention relates to the genetic differentiation of individual plant isolates and varieties using restriction enzyme technology.

2. State of the Art

A long-standing problem which has plagued plant breeders is the inability to distinguish closely related isolates with any certainty. Both individual and varietal identification are important for a number of purposes including plant breeding and hybridization and patent protection. Effective problem solving in these areas has been severely complicated as it can rarely be demonstrated that one isolate is not just closely related to another, as opposed to being a derivative of it or even an identical isolate.

Presently, differentiation of individual plants or plant varieties is usually accomplished by visual inspection. The two major disadvantages of visual inspection are (a) often there are not enough definitive visual characteristics between closely-related individual plants to make a positive differentiation, and (b) the visual characteristics are greatly affected by environmental factors.

Typical characteristics used in establishing distinctiveness have included habit, immunity from disease, soil condition, color, flavor, productivity, storage qualities, perfume and form. The International Union for the Protection of New Varieties of Plants (UPOV) recommends that competent authorities use the characteristics of color of tuber skin, color of the base of the sprout, color of the tip of the sprout, existence of flowers, color of the inner and outer sides of petals, tuber shape and contour, sprout shape, and stem coloration for the grouping of plant varieties.

Obviously, non-related individual plants may be so visually different that differentiation based on such characteristics is easily accomplished. However, closely-related, yet different, varieties as well as similar progeny in a breeding program will possess many similar structural characteristics which make their distinction by these characteristics nearly impossible. Furthermore, because of the many heritable genes that go together to actually compose a plant's visual appearance and economic characteristics, differences in any one particular gene are often so diffused by the total mass of characters that it cannot be isolated for use as a differentiating characteristic for varietal distinguishment.

Even when sufficient visual characteristics are available to determine individual and varietal differences, they are often unreliable as they are subject to environmental effects. A heritable visual characteristic is usually the result of a phenotypic expression of different plant genes. Often the phenotypic expression of a gene is substantially influenced by environmental factors such as temperature, water condition and amount, soils, amount and intensity of light, available nutrients, etc. This large variation in phenotypic expression may cause severe confusion when the plants are grown under different conditions, as between the distinguishment of plant varieties and the mere recognition of the range of phenotypic expression within a single variety.

Alternatives to visual characteristics for individual and varietal distinguishment have been proposed. One such approach is based on differentiating chemical phenotypic expression through isozyme analyisis. Isozymes are enzymes which have similar biological activities, but have different amino acid sequences. The differences in amino acid sequence indicate that the isozymes originate from different genotypes. Isozyme analysis typically involves the steps of isolation and partial purification of the isozymes of interest with detection of amino acid sequence differences by such techniques as starch gel electrophoresis.

If different isozymes are detected in two different plant isolates, it can always be concluded that they are not genotypically identical. A summation of the similarities and differences between two such isolates can even serve to indicate their overall relatedness. The converse, unfortunately, cannot be concluded. Different plant varieties may not necessarily possess different isozymes. Therefore, one of the major problems with the application of isozyme technology to identification is again the lack of sufficient numbers of variants in closely-related lines to positively distinguish them. In addition, since the isozymes are phenotypic expressions of genes, they are still affected by environmental factors or might only be specific to certain plant tissues.

To avoid the effects of environmental factors and also to have positive identification, one could concentrate on genotypic rather than phenotypic differences. A summation of detectable differences between individual plants in their deoxyribonucleic acid (DNA) sequences could be used as "fingerprints" for estimating the relatedness of those individual plants. Although the technology presently exists to actually sequence DNA, it is not applicable to this problem for practical reasons as it requires a great deal of time and effort to sequence even one short segment of DNA, and this type of analysis would require sequencing many segments from each of many individuals.

Instead of actual DNA sequencing, the present applicants apply restriction fragment technology to detect genomic DNA sequence differences to define relatedness. Although restriction fragment technology and the polymorphisms thus identified have been used to construct genetic linkage maps in humans and other species, it has not been applied to problems in plant science nor developed to detect either varietal differences or homozygosity. The adaptation and application of restriction fragment technology to detect both the degree of relatedness and homozygosity in plants is the essence of the present invention.

SUMMARY OF THE INVENTION

It is, therefore, a general object of the present invention to provide a method for determining the degree of relatedness or identity/non identity between isolates which is not affected by environmental factors and which is highly reliable for the purposes of plant variety identification.

It is another object of the present invention to provide a method of detecting differences between isolates which takes a short time to perform and uses a relatively small portion of the plant specimen, whereby the plant may be further used for other purposes.

It is another object of the present invention to provide a method for determining the relatedness of potential parents in a hybrid cross for optimizing the success of the hybrid progeny.

It is another object of the present invention to provide an analysis to evaluate the relatedness between individual progeny and parent material in a breeding program to speed up that process.

It is another object of the present invention to provide a method for determining the degree of homozygosity of individual plants in a breeding program.

It is another object of the present invention to provide a mechanism for determining the linkage of a trait of interest with a restriction fragment and thus provide a tool to determine if a particular trait has been inherited during a breeding program.

In accordance with the above objects, the present invention provides a method that includes the steps of cloning DNA probes; evaluation and selection of useful probes; labeling of the probes; preparation of plant DNA to be tested; restriction of the test DNA; electrophoresis of the restriction fragments; transfer of the electrophoresed DNA onto a suitable hybridization matrix; hybridization of restriction fragments with the labeled probes; detection of the hybridization product; repeating the above steps a sufficient number of times with various restriction enzymes and probes to build up a unique genomic DNA genetic map "fingerprint" for the test plant; and comparing the test plant genomic "fingerprint" to genomic "fingerprints" prepared for other varieties or isolates to determine both the degree of relatedness and homozygosity.

BRIEF DESCRIPTION OF THE DRAWINGS

The drawings illustrate that which is presently regarded as the best mode for carrying out the invention:

FIG. 2, a schematic illustration of restriction enzyme mechanisms;

FIG. 3, a schematic illustration of gel electrophoresis;

FIG. 4, an illustration of an apparatus for Southern transfer;

FIG. 7, a schematic representation of a resulting autoradiogram of thirteen individual C103 corn plants.

DETAILED DESCRIPTION

Figure 1:
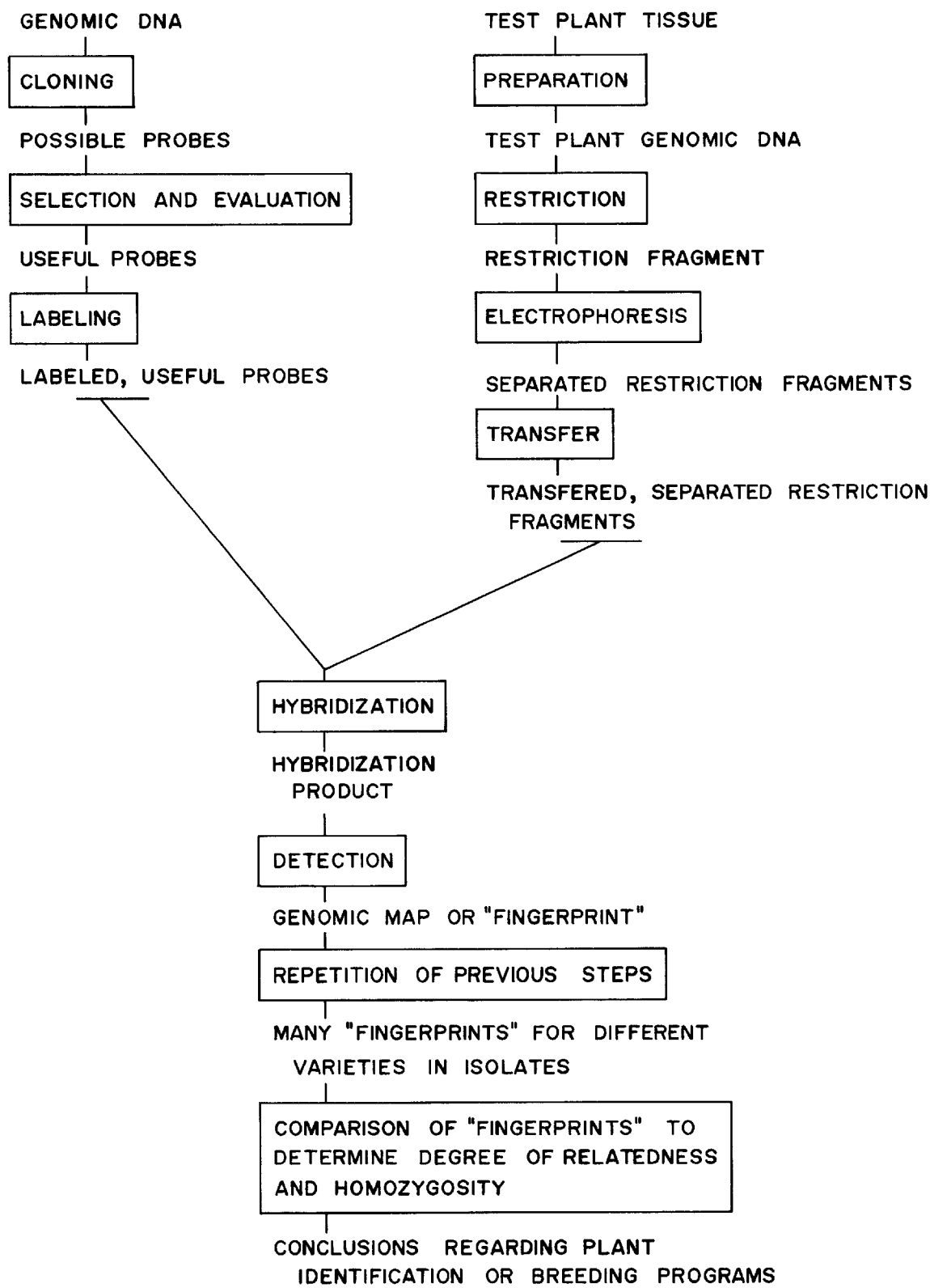
FIG. 1 is a schematic block diagram outlining the steps of the invention.

FIG. 1 is a block diagram schematically illustrating the eleven steps of the invention, including: 1) cloning of DNA probes; 2) evaluation and selection of useful probes; 3) labeling of the probes; 4) preparation of plant DNA to be tested; 5) restriction of the test DNA; 6) electrophoresis of the restriction fragments; 7) transfer of the electrophoresed DNA; 8) hybridization of restriction fragments with labeled probe; 9) detection of the hybridization product; 10) repetition of steps 1 through 9 with different restriction enzymes and probes until a sufficient genomic "fingerprint" of the variety or isolate being characterized is established; and 11) comparison of the genomic "fingerprint" with genomic "fingerprints" of other individual plants and varieties, which have been established in the same way, to determine the degree of relatedness or identity of individuals or varieties.

It should be understood that Steps 1 through 3 and 4 through 7, as clusters of steps, do not have to follow one another. In other words, Steps 4 through 7 may be performed before or at the same time as Steps 1 through 3. Each of the eleven steps will now be addressed individually, and it should be understood that the particular laboratory parameters such as chemicals, reagents, heat, temperature, and time, etc., used in each step may vary within the scope of this disclosure for application of the invention to different plant species. A specific example of the invention as applied to corn is discussed fully under the heading "EXAMPLE" hereinbelow.

In Step 1, cloning of DNA probes, several existing standard techniques for the cloning of DNA fragments in either plasmid or phage vectors will work equally well. In the Example, plant genomic DNA from which the probe is to be made is digested with one or more restriction enzymes. To clone the resulting restriction fragments into a plasmid vector, plasmid DNA is cleaved with a similar restriction endonuclease and joined in vitro to the ends of the restriction fragment with a DNA ligase. Alternatively, a cDNA copy of plant mRNA could be cloned and used. All that is required is a cloned DNA fragment which hybridizes with that plant's genomic DNA. The resulting recombinant DNA is used to transform bacteria. Colonies of the transformed bacteria are then grown on a suitable media which will differentiate between these bacteria which have been transformed with DNA containing a restriction fragment and those which merely contain plasmid DNA which has recircularized without insertion of a restriction fragment. This differentiation is usually achieved by observing a change in drug resistance between bacteria which have been transformed with recircularized plasmid DNA and those which have been transformed with plasmid DNA containing a fragment insertion. The colonies containing clones may then be picked for use in Step 2 at random since the identity or function of the DNA fragment used as a probe is unimportant to this analysis. However, specific, identified clones may also be used in this analysis, and may be especially useful in some cases. Cloned fragments from other species or genera may also be used as long as they cross-hyridize with the plant DNA of interest.

In Step 2, evaluation and selection of useful probes, the clones are screened for size of the cloned insert and for non-repetitiveness of the probe DNA sequence within the test plant genomic DNA. For optimum hybridization results, for performance of Step 8, the cloned insert should be within a reasonable size range, preferably greater than 300 base pairs; and to produce a clean "fingerprint" which is not smeared, the probe must be of low copy number.

Screening of the colonies is accomplished with three screening procedures. The first procedure is a screen for clones which indicates that the cloned insert sequence is present in less than one hundred to two hundred copies within the test plant DNA. This is accomplished by hybridizing the clones with phosphorus-32-labeled total genomic DNA prepared from any variety of the plant types to be eventually tested. A hybridization in which a clone shows no signal on an autoradiogram when controls provide adequate signal indicates that the cloned sequence is present in less than one hundred to two hundred repetitions per genome. This first screening procedure is performed at least once and clones showing less than one hundred to two hundred copies, i.e. no hybridization signal, are selected for the second screening procedure.

The second screening procedure is based on insert size. Purified DNA from colonies containing plant DNAs which pass the first screening procedure is electrophoresed on an agarose gel along with plasmid vector DNA containing no fragment insert as a molecular size reference. Those clones which show a greater than three hundred base pair insert are carried on to the third screening procedure.

The third procedure is a further screen for low copy number and is probably sensitive enough to show less than twenty copies per test plant genome. Individual cloned DNAs are mixed with radioactively-labeled vector DNA, as explained in Step 3 hereinbelow. The mixtures of cloned DNA and labeled vector DNA are then hybridized with small amounts of plant genome DNA and a graduated dilution series of the plasmid vector DNA. Depending upon the average size of the insert (about 1000 base pairs in this case) and the total number of base pairs in the plant genome, a comparison of the level of hybridization signal to the genomic DNA, with that signal of the vector DNA dilution series, will indicate a low copy probe, ie., less than twenty repetitions of the probe nucleotide sequence in the test plant genome.

Depending on the particular purpose for the polymorphism, a single copy or a low repetitive sequence may be more desirable. For example, if the aim of a particular test is to determine relatedness between plants, then a repetitive probe which produces distinct bands on an autoradiogram will be more useful than a single copy probe because one probe will provide numerous reference points. If the aim is to link a particular probe with a trait of interest, then a single copy probe may be required as repetitive probes are more difficult to localize to specific areas of the genome. An illustration of this step and the calculations involved, is shown in the "Example" of a specific variety hereinbelow.

Step 3, labeling of the genomic probe, may be accomplished by a number of well established procedures. Nick translation as well as in vitro reverse transcription may be used. The preferred method is using reverse transcriptase enzyme random primers and $^{32}P$ labeled precursor bases. In practice, the DNA is placed into a test tube and denatured into separate strands. The denatured DNA is then mixed with the appropriate buffer, random primers, phosphorus-32 labeled deoxytriphosphates of one or all bases (dXTP's-$P^{32}$), and reverse transcriptase. The random primers mate to the appropriate matching base pairs on the denatured strands. The reverse transcriptase then transcribes, by reading the rest of the denatured DNA strand, filling in the missing portions of the DNA strand between the random primers with the dXTP's-$P^{32}$. In this way, a radioactively-labeled DNA copy is produced with the dXTP's-$P^{32}$.

Step 4, preparation of the genomic plant DNA to be tested, may be achieved by a number of DNA preparation procedures as long as such produce useable genomic plant DNA. Useable plant DNA, for the purpose of the invention is isolated plant DNA which has not been extensively sheared (i.e. pieces are larger than 30,000 base pairs) and can be digested by most restriction enzymes. For example, one procedure that has been used in Step 4 is that reported by Kislov and Rubenstein, 1980, *Plant Physiology* 66:1140–1143. This procedure produces a low yield of nuclear DNA which is relatively free of either mitochondrial or chloroplast DNA. A procedure that is the preferred procedure for corn as is detailed in the "EXAMPLE" hereinbelow, is that reported by Pelaposta, Hicks, Chonet, and Mettinger, in an article in preparation for the *Plant Molecular Biology Newsletter.* This procedure produces a high yield of useable DNA which contains a plastid DNA contaminant. The contamination, however, does not interfere with the invention.

Step 5, restriction of the genomic DNA, involves the genomic plant DNA which was prepared and isolated in Step 4 and is digested to completion with various restriction enzymes according to the enzyme manufacturer's instructions. Restriction enzymes are a class of enzymes which will digest large pieces of DNA, from any source, into smaller fragments of DNA by cutting the larger pieces at a particular sequence of nucleotides, that sequence being characteristic for each enzyme. For example, Eco Rl, the first restriction enzyme isolated, will cut double-stranded DNA only at sites containing the nucleotide sequence 5'GAATTC3'. Under the proper conditions, it will not cut DNA at any other sequence of nucleotides, no matter how similar such is to the specified sequence. Many other such enzymes have been isolated, most with quite different restriction sites such as Hind III, which cuts at the nucleotide sequence 5'AAGCTT3'; Bgl II, which cuts at the nucleotide sequence 5'AGATCT3'; or Hae III, which cuts at the nucleotidetide sequence 5'GGCC3'.

The mechanism of these enzymes is schematically illustrated, in a very simplified form, in FIG. 2. Therein, the solid horizontal black bar 11 represents a small section of the total genomic DNA of an organism. The vertical lines 12 that vertically intersect the top of the solid black bar represent the cut sites for a particular restriction enzyme E, and the vertical lines 13 that intersect the bottom of the black bar represent the cut sites of a different restriction enzyme B. In other words, the vertical lines show where, in the small section of total genomic DNA, the particular nucleotide sequences occur that the restriction enzymes E and B are specific for. Thus, digestion of the small section of genomic DNA by enzyme E results in restriction fragments $E_1$, $E_2$, $E_3$ and $E_4$ of varying nucleotide lengths, and digestion of the same small section of genomic DNA by restriction enzyme B results in restriction fragments $B_1$ and $B_2$.

The restriction fragments produced in Step 5 are then separated in Step 6, electrophoresis of the restriction fragments, by agarose gel electrophoresis. Agarose gel electrophoresis is a commonly used technique to separate large biomolecules by size. In practice, samples of the restricted DNA are placed at one end of an agarose gel slab. The slab is submerged in a buffer and an electric current is then applied across the two ends of the slab. The electric current causes the DNA fragments to migrate through the slab at a rate which is inversely proportional to fragment size. Fluorescent dyes may be added to the fragments so that their migration may be observed under ultraviolet light. The resolution of a combination of fragments of various sizes depends on the variable parameters of agarose concentration in the gel slab, strengths of the applied current, type of buffer used, and amount of restriction fragments placed on the slab. A particular set of parameters is set forth for corn in the "EXAMPLE" hereinbelow.

To further illustrate agarose gel electrophoresis, FIG. 3 schematically represents two lanes 14 of an agarose gel slab which have been loaded with the restriction fragments resulting from the digestion of the DNA by restriction enzymes E and B, from FIG. 2, and the gel electrophoresed for a period of time under appropriate conditions. The horizontal bars 15 of FIG. 3 represent the different fragments after staining with with an ultraviolet fluorescent dye and as viewed under ultraviolet light. As seen from FIG. 3, the larger fragments have migrated a shorter distance through the gel than the smaller fragments.

It should be noted that FIGS. 2 and 3 illustrate the concepts of restriction enzyme digestion and electrophoresis of the restriction fragments in a very simplistic way. In reality, an entire plant genome might contain from $1 \times 10^9$ to $10 \times 10^9$ base pairs and the restriction enzymes currently commercially available produce fragments that average $4 \times 10^2$ to $4 \times 10^3$ base pairs in length. Thus, on an average, as many as one million different restriction fragments would be produced in a digestion of the entire genomic DNA. Since the typical agarose gel slab is less than twenty centimeters in length, this multitude of separated and stained fragments appear visually as a smear when viewed under ultraviolet light. To resolve a particular group of separated fragments from the smear of fragments, the smear is hybridized with the labeled genomic probe, prepared in Steps 1, 2, and 3 and the hybridization product is detected through autoradiography. The autoradiogram will show the location of any bands of restriction fragments which are complementary to the labeled genomic probe. As set out below, Steps 7, 8, and 9 achieve these goals and produce the autoradiogram or "fingerprint" of the genomic plant DNA tested.

In Step 7, transfer of the electrophoresed DNA, the separated DNA restriction fragments from the agarose gel are transferred onto a matrix suitable for carrying out the hybridization of the fragments with the labeled probe. A number of standard blotting techniques can be used for this step. However, the preferred technique is known as Southern Transfer. This technique was developed by Southern (E. M. Southern (1975) J. Mol. Bio. 98: 503–517), and involves using a suitable transfer buffer to elute the DNA restriction fragments onto a suitable hybridization matrix.

FIG. 4 illustrates a typical arrangement used in Southern Transfer. In practice, a transfer buffer 16 is placed in a vessel 17 of suitable size. A sponge 18, of the same dimension or larger than the DNA fragment containing agarose gel slab, is then saturated with the transfer buffer and placed in the center of the vessel to act as a wick for the transfer buffer to flow upwardly through. On top of the sponge are placed at least two sheets of a suitable filter paper 19 cut to the same dimensions as the agarose slab. On top of the filter, the fragment containing agarose slab 20 is placed such that the top side, during electrophoresis, is in contact with the filter paper. On top of the agarose slab is arranged the hybridization matrix 21, followed by at least two more sheets of suitable filter paper 22, a stack of paper towels 23 to absorb the upflowing transfer buffer, and a weight 24 to compress the underlying layers into close contact with each other. All layers of the transfer apparatus should be cut to the dimensions of the agarose slab to prevent "short circuiting" of the transfer buffer around the outer edges of the agarose slab. The transfer buffer is then allowed to flow up through the agarose slab and hybridization matrix for a period of time sufficient to transfer the DNA fragments to the hybridization matrix. After transfer is complete, which can be checked by viewing the agarose slab under ultraviolet light to see if any stained DNA fragments remain in the slab, the transferred DNA fragments are then fixed to the hybridization matrix by air drying and baking in a vacuum oven. If the transferred DNA fragments are not immediately to be used in hybridization experiments, they may be washed, air dried, and stored in an air-tight container at 4° C.

After the DNA restriction fragments are transferred to the hybridization matrix, the fragments are hybridized with a labeled probe, as set out in Step 8. In Step 8, hybridization of restriction fragments with labeled probe, the restriction-fragment containing the hybridization matrix is typically soaked in an appropriate hybridization buffer which serves to neutralize any non-specific sites on the matrix where the probe might bind, and to furnish a suitable ionic environment for specific hybridization to the proper covalently-bound genomic DNA sequences. The labeled probe is added and allowed to hybridize with the restriction fragments for an appropriate period of time. Thereafter, the unbound probe is rinsed away. The specific parameters of hybridization, such as hybridization buffer, length of time and temperature of prehybridization, and length of time and temperature of hybridization, will change with the type of restriction fragments, cloned probes, and amount of probe used. A specific set of parameters to carry out Step 8 for corn DNA is set forth in the "EXAMPLE" hereinbelow.

After hybridization of the restriction fragments with labeled genomic probe, the hybridization product is detected, as set out in Step 9, detection of hybridization product. In one detection technique, for practicing Step 9, an autoradiogram of the hybridization product is prepared. The autoradiogram is preferably prepared by wrapping the hybridization matrix containing the hybridization product in some type of plastic wrap, such as Saran Wrap®, and applying it to an X-ray film for a sufficient exposure time to obtain an autoradiographic image of the labeled probe that will have hybridized with the restriction fragment bands. The resulting autoradiogram is a genomic "fingerprint" of the particular plant DNA tested. Each DNA restriction fragment band represents a unique cloned DNA sequence which may exhibit polymorphism and may be correlated with a specific characteristic of interest in a plant to server as a maker for plant identification or for use in breeding strategies.

Step 10, repeating Steps 1 through 9, is practiced with different restriction enzymes and probes until a sufficient "fingerprint" of the variety or isolate is established. A sufficient genomic "fingerprint" of a particular variety or isolate is one which would uniquely identify the genomic DNA of the variety or isolate. The uniqueness of a genomic "fingerprint" is a relative term. Individual uniqueness would be that which would distinguish those individuals to be tested. In a breeding program, probes which distinguish between the parents in a cross would also distinguish the inherited chromosomal segments in the progeny and, hence, also establish the overall relatedness of any particular progeny to either of the original parents. The probes could also be used to determine the level of homozygosity in these progeny since they distinguish between chromosomal segments inherited from each parent. Varietal uniqueness, on the other hand, would be a "fingerprint" which would be unique enough to distinguish DNA sequence differences between two different varieties, but not so unique as to differentiate between individuals within a variety. For the purposes of this invention, a varietal "fingerprint" constructed in Step 10 would be one in which the possible number of differences should be at least equal to or greater than the possible number of different varieties to be eventually tested. For example, if only two varieties of a plant were possible, only one difference might be necessary to separate them; if there were four, only four distinguishing DNA restriction fragments should be necessary, one for each variety. The more DNA restriction fragments the more positive the identification and since there is an almost unlimited number of these types of DNA restriction fragments, which are easier to isolate than previous types, it is possible to use a number of DNA restriction fragments several times larger than the probable number of varieties.

Step 11, is a comparison of the genomic "fingerprint" established in Step 10 with the genomic "fingerprints" of other individual plants or varieties, which have been established in the same way, to determine the degree of relatedness or identity of individuals or varieties. The differences in these genomic "fingerprints" which define the degree of genetic similarity are restriction fragment polymorphisms.

Comparison between the occurrence of a particular characteristic of interest in a plant species and the "fingerprint" of individual isolates by computer analysis will suggest which random clones are linked to the genes of interest. Further examination of a statistically significant number of plants will substantiate the degree of linkage between the clone and the trait. For example, resistance to a particular disease may then be correlated to the inheritance of a particular DNA fragment and this particular fragment may then be used as a marker for that trait.

Figure 5:
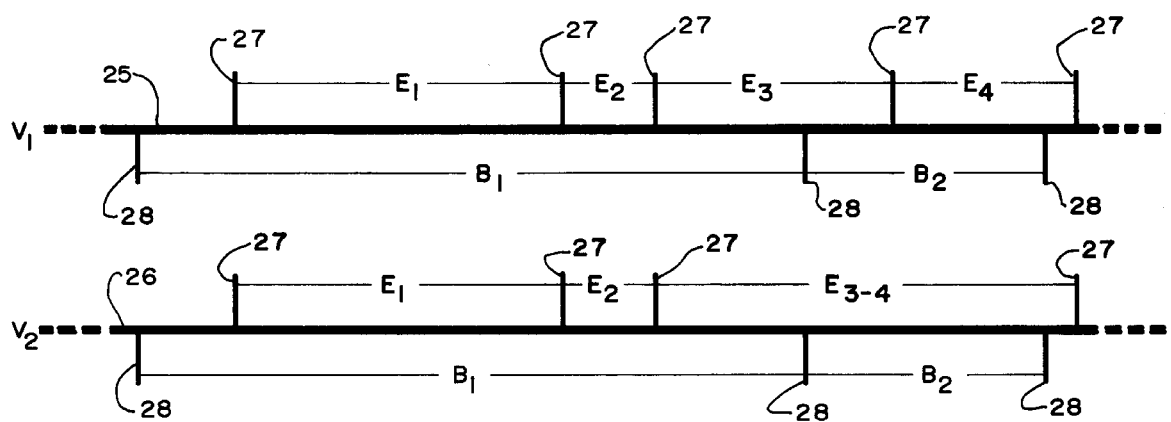
FIG. 5, a schematic illustration of and the effect of DNA sequence differences on restriction fragment sizes.
Figure 6:
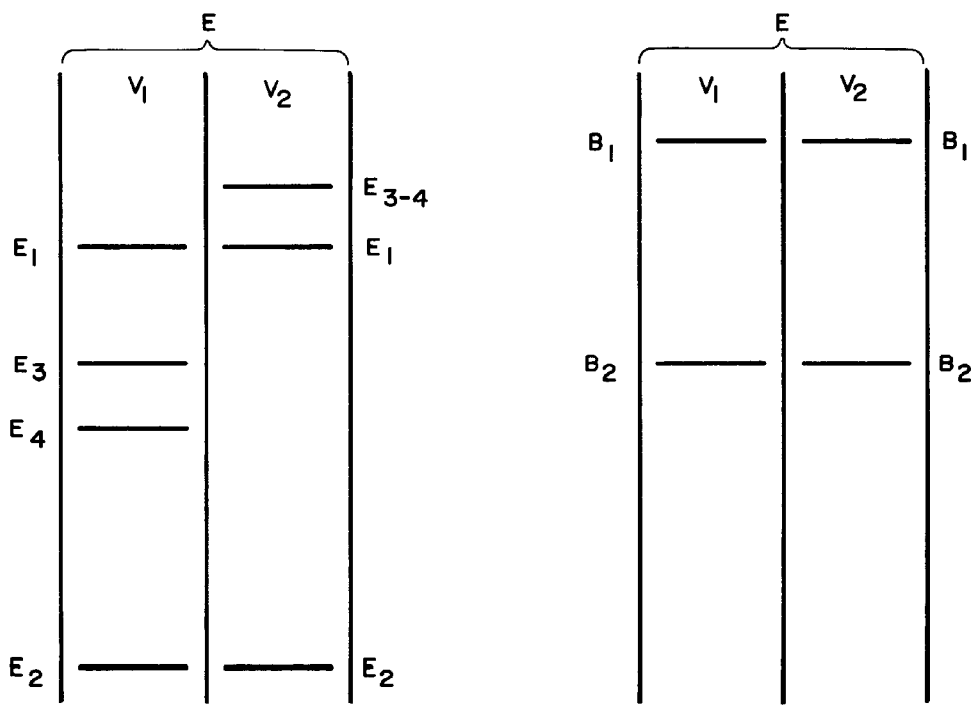
FIG. 6, a schematic illustration of the detection of restriction fragment differences.

Restriction fragment polymorphism is illustrated schematically in FIGS. 5 and 6. Referring to FIG. 5, horizontal lines 25 and 26 represent genomic DNA of two closely related varieties, $V_1$ and $V_2$, respectively. Lines 27 are shown intersecting the top lines 25 and 26 at right angles to represent specific cut sites of a restrictive enzyme E on the genomic DNA sequences $V_1$ and $V_2$, and lines 28 are shown intersecting the bottom lines 25 and 26 at right angles to represent specific cut sites of a restriction enzyme B on the genomic DNA sequences of $V_1$ and $V_2$. As shown, restriction enzyme E produces restriction fragments $E_1$, $E_2$, $E_3$, $E_4$; and $E_1$, $E_2$, $E_{3-4}$ from the genomic DNA of $V_1$ and $V_2$, respectively. It is also shown that restriction enzyme B produces restriction fragments $B_1$ and $B_2$ from the genomic DNA of both $V_1$ and $V_2$.

Referring to FIG. 6, the portions labeled E and B represent autoradiograms of a radioactively-labeled probe which has been hybridized to restriction fragments formed by treating genomic DNA of varieties $V_1$ and $V_2$ with the restriction enzymes E and B, according to Steps 1 through 9 of the invention. As can be shown in the B autoradiogram of FIG. 6, enzyme B has produced the exact same restriction fragments from $V_1$ and $V_2$. Therefore, the B autoradiogram indicates a lack of genomic DNA differences or restriction fragment polymorphisms between varieties $V_1$ and $V_2$ when the varieties are treated with the restriction enzyme B and the same radioactively-labeled probe.

Autoradiogram E of FIG. 6 shows that application of the restriction enzyme E produces different restriction fragments from the genomic DNA of varieties $V_1$ and $V_2$. This indicates that there are genomic DNA differences, or restriction fragment polymorphisms between varieties $V_1$ and $V_2$ when the varieties are treated with restriction enzyme E and hybridized with the same probe. Since restriction enzyme E produced fragments $E_3$ and $E_4$ in $V_1$, but only the fragment $E_{3-4}$ in $V_2$, it can be deduced that one or more nucleotide sequence differences have occurred at the $E_3$–$E_4$ nucleotide junction such that restriction enzyme E will no longer cut the nucleotide sequence in $V_2$ at that junction. Therefore, restriction enzyme E and the specific radioactively-labeled probe used to detect the restriction fragments produced by enzyme E clearly separates $V_1$ from $V_2$ based on DNA nucleotide sequence differences, as reflected in the observed restriction fragment polymorphisms.

With a number of such detectable nucleotide sequence differences between individual plants or varieties, a genomic DNA "fingerprint" may be established, as outlined in Step 10, for any particular individual plant. If two individual plants are highly unrelated, their genomic DNA nucleotide sequences will be very different and, therefore, their genomic "fingerprints" will be very different as there will be many detectable restriction fragment polymorphisms. The more related two individual plants or varieties are, the more alike their genomic DNA sequences will be and, therefore, their genomic "fingerprints" will have fewer points of dissimilarity as there will be fewer detectable restriction fragment polymorphisms. However, no matter how related two individual plants are, if they are truly two separate isolates or varieties, there should still be a significant number of dissimilarities in their genomic "fingerprints", provided the correct restriction enzymes and labeled probes are used to detect the DNA sequence differences between the isolates.

The number of points of dissimilarity to establish non-relatedness to define a variety for the purposes of this invention is dependent on the number of varieties available within the judgment of the testers. From the varieties available, a minimum number of characters can be determined to test new varieties for identity. If a new isolate appears quite similar to a previous one, another group of restriction fragment length polymorphisms can thus be applied to it and the similar variety to determine identity. A procedure for selecting the number of restriction fragment length polymorphisms required to establish identity for a variety of corn is set out in the Example with corn. In practicing the procedure, initially a screen with between 300 and 500 characters is set up. In such screen, possibly 50% of these restriction fragment length polymorphisms may not be different between any varieties of a plant that one chooses to test, but they will be different for every other plant type, ie. that part of the "fingerprint" that defines a particular plant. A larger percentage of the rest of the characters will vary, with the percentage of such variation based upon the relatedness of the two varieties to be compared. For example, closely related varieties might differ in only 5% of the characters tested while more distantly related varieties might differ over as much as 5–50% of their restriction fragment length polymorphisms, or even more.

To handle the problem of individual variation within a variety, two protocols are possible. First, this variation should be rather small and a lower limit of 1–2% can be set. Thereby, differences of less than 1–2% would be due to individual variation as opposed to actual varietal differences. Isolates showing approximately 2–5% variation can be retested with even more restriction fragment length polymorphisms, 500 or more to significantly increase the statistical probability of the result. A second approach would be to test a larger group of plants, as say from six to twelve. This would dilute out the natural residual variation within a population to an undetectable level and form a "consensus fingerprint" for that variety. This approach is quite easy and may even be necessary for open pollinated plants as opposed to inbred varieties. In practice of the present process, both approaches are combined. The testing, as used in the corn Example, would consist of 300–500 DNA restriction fragments. Isolates showing greater than 5% differences would be considered to be definitely different. Those with variation of 2–5% were retested with another 300–500 DNA restriction fragments. If this level of variation held up, then they would be presumed to be different, but closely related. Levels of 1% or less difference would be considered to be extremely closely related varieties but, in actuality, should be considered isolates of the same variety.

Once the number of points of dissimilarity to define a particular variety is defined from a varietal genomic "fingerprint", a new isolate's genomic "fingerprint" may then be derived by using the same combination of restriction enzymes and labeled probes as was used to derive the variety's genomic "fingerprint". The new isolate's genomic "fingerprint" may then be compared against the variety's genomic "fingerprint" to determine if the isolate is of the same variety or of a new or different variety. Since these genomic "fingerprints" are derived directly from DNA nucleotide sequence differences, varieties are identifiable independent of environmental factors and the other variable parameters which have made previous methods of varietal identification unreliable.

Genomic "fingerprints" which define the unrelatedness of genomic DNA of different varieties are also useful for breeding purposes. It is thought that the successfulness of the progeny of an inter-varietal hybrid cross is related to the degree of unrelatedness in the parents in the cross. In other words, the chance that the progeny of two parents in a hybrid cross will demonstrate heterosis or hybrid vigor increases if the parents are highly unrelated. Since the genomic "fingerprints" derived by a practice of the invention directly show the degree of relatedness between two potential parents to a hybrid cross, the genomic "fingerprints" can be used to screen potential parents to obtain the best cross. Since the invention uses a minute quantity of an individual plant to construct a genomic "fingerprint", the parents may be evaluated while still at the seedling stage of development. This saves a great deal of time and resources in breeding programs as the traditional methods of evaluation require mature plants. Moreover, evaluation using the invention is a more reliable indication of unrelatedness than the traditional methods of evaluation, which are subject to environmental factors and other non-controllable parameters.

Another use of the process of the invention is in a breeding program to test for relatedness as for crossing a useful trait from an outside source into an otherwise very good variety. Such a cross could be made and the progeny screened in the field or a laboratory for the presence of the useful trait. A number of such progeny could also be screened by the invention for the most overall relatedness to the good variety. Those progeny, showing both the useful trait and a high degree of relatedness to the useful variety, could then either be back-crossed to the useful variety to eventually recreate it and to provide the addition of the useful trait.

An additional use for the invention is based on the fact that one can detect not just the phenotype of an isolate but also its genotype. Homozygosity is an essential character in the breeding of both hybrids and varieties. In crossing different lines to produce a new line, the presence of the different parental alleles is clearly detectable by the invention. By screening and selecting progeny for most homozygosity (i.e. the presence of only one parental type allele at any locus), one could significantly speed up the inbreeding process.

The invention is further described in connection with the following example which is intended to illustrate the invention, but not to limit the scope thereof. It should be understood that the following example, utilizing varieties of corn, is organized around the eleven basic steps of the invention as outlined above. However, each of these basic steps may contain a number of substeps needed to technically carry out a basic step. While some of the substeps may directly work for other plant species besides corn, other substeps may need to be adjusted or changed slightly to achieve the same technical result. The technical changes required to adapt the invention to any species of plant are considered easily within the capabilities of one skilled in the art of the invention.

EXAMPLE

Corn

Practicing Step 1, cloning of DNA probes, the fragments are produced by cutting approximately 100 ug of genomic DNA from the corn variety Hy2 with approximately 400 units of restriction enzyme BamHI according to the manufacturer's specifications. A unit is the amount of enzyme needed to perform the specified enzymatic activity on one microgram of substrate in one hour's time. BamHI restriction enzyme cuts at the sequence $5'GGATCC^{3'}$ between the GG junction. The restricted Hy2 DNA is then precipitated with ethanol and spun in a centrifuge into a pellet which is then suspended in deionized water. The restricted Hy2 DNA is then further cut with the restriction enzyme TaqI according to the manufacturer's specifications to produce restriction fragments with proper end nucleotides for later ligation to the plasmid vector DNA. TaqI restriction enzyme cuts at the sequence $5'TCGA^{3'}$ between the TC junction. The resulting restriction fragments are then loaded onto a 1.2% Seaplaque® agarose gel slab and electrophoresed to separate the fragments by molecular size. The section of the gel containing fragments of DNA 500 to 2,000 base pairs in length is surgically removed from the rest of the agarose slab. To isolate the DNA from the agarose gel, the excised agarose is placed in a solution containing 5 ml of 1M tris (hydroxymethyl)aminonethane-HCl (Tris-HCl) at pH 8.0, 2 ml of 0.5M ethylenediamine tetraacetic acid (EDTA), 5 ml of 5M NaCl, 5 ml of 20% sodium dodecyl sulfate (SDS), and 9 ml of deionized water. The agarose is then melted by heating the solution to 68° C. and the restriction fragments are extracted one to two times with phenol and then one to two times with chloroform. The restriction fragments are then precipitated with ethanol, spun into a pellet and resuspended in TE, which is 10 mM Tris pH 8.0, 1 mM EDTA.

Circular DNA from the bacterial plasmid pBR322 is prepared for ligation by cutting 50 ug of the plasmid DNA with BamHI according to the manufacturer's specification to create one of the proper ligation sites. The cut plasmid DNA is then precipitated with ethanol, spun into a pellet, and resuspended in deionized water. The plasmid DNA is then further cut with the restriction enzyme ClaI to create the other ligation site and to inactivate tetracycline resistance by disruption of the gene which codes for resistance. ClaI restriction enzyme cuts the sequence $5'ATCGAT^{3'}$ at the TC junction. The twice cut plasmid DNA is then electrophoresed on an agarose gel to isolate plasmid DNA that is missing the nucleotide sequence and which codes for tetracycline resistance. The isolated plasmid DNA is then recovered from the agarose gel slab as outlined above for the restriction fragments.

5 ug of the Hy2 restriction fragments are then ligated to 5 ug of the twice cut plasmid DNA by first suspending both types of DNA in a solution which is 66.6 mM in Tris HCl at pH 7.5, 10 mM dithiothreitol (DTT), and 6.6 mM in $MgCl_2$. The suspension is then heated to 65° C. for 2 minutes and chilled on ice. The suspension is then brought to be 1 mM in adenosine 5'-triphosphate (ATP) and two units of T4 ligase from BRL® are added. The degree of ligation is then checked on an agarose gel using a small amount of the recombinant plasmid DNA product.

The recombinant DNA is then used to transform bacteria by the heat shock transformation procedure of Mandel and Higa, *Journal of Molecular Biology* 53:159(1970). An appropriate bacteria culture, preferably a culture of *Escherichia coli*, TR105, or K84 is grown overnight and then one to ten dilution subcultures are allowed to grow for two hours at 37° C. The subcultures are chilled on ice, centrifuged, resuspended in 10 ml of 0.1 M $MgCl_2$, centrifuged, resuspended in 5 mls of 0.1M $CaCl_2$, kept on ice for thirty minutes, centrifuged, and resuspended in 1 ml of 0.1M $CaCl_2$. To 0.2 ml of this final 1% cell solution the recombinant plasmid DNA is added and the bacteria are then chilled on ice for thirty minutes. The bacteria are then heat shocked by bringing them to 42° C. for two minutes and then rechilling them on ice. After the addition of 2.7 ml of a prewarmed solution which is prepared by mixing 10 g of Bacto-Tryptone, 5 g of yeast extract, 10 g of NaCl, and one pellet of NaOH in a 1 liter final volume of deionized water, the cells are incubated at 37° C. for 30 minutes. The bacteria are then plated out on agar and grown into colonies. The colonies are then checked for tetracycline resistance or sensitivity. Those colonies showing tetracycline sensitivity are the colonies of bacteria which have been transformed with recombinant DNA and not with recircularized pBR322 plasmid vector DNA.

Since the tetracycline sensitive colonies are the ones most likely to contain clones of Hy2 restriction fragments, those colonies are selected for practicing Step 2, evaluation and selection of useful probes. The colonies are first screened twice to eliminate clones whose sequence appears more than 100 to 200 times in the test plant DNA. This is accomplished by fixing the clone DNA to a suitable hybridization matrix, prehybridizing the DNA for an appropriate period of time, hybridizing the DNA to labeled total corn DNA, and preparing an autoradiogram of the hybridization products. Colonies with no hybridization signal on the autoradiogram are selected for further screening since this indicates less than 100 to 200 copies of the cloned sequence per corn genome. It also discriminates against most plastid DNA fragments.

Clones passing the first screen for multiple copies are then screened for size of the inserted DNA. First, the DNA is recovered from the colonies and partially purified. The DNA is recovered from the colonies by centrifuging the bacteria into a pellet and resuspending the pellet in 350 ul of a solution containing 8% sucrose, 250 ul of 10% triton, 1 ml of 0.5M EDTA, 100 ul of 1M Tris HCl pH 8.0, and 8.65 ml deionized water. To this suspension 25 ul of 10 mg/ml (in TE) lysozyme is added and the suspension is mixed with a vortex mixer. The suspension is then heated in a boiling water bath for a sufficient period of time to digest the bacterial cell walls without damaging the DNA. The suspension is then centrifuged to remove particulate matter. The supernatant is then treated with 40 ul of 2.5M sodium acetate and 420 ul of isopropanol, and chilled on ice for fifteen minutes to precipitate the cloned DNA. The precipitate is then collected by centrifuging for five minutes and the pellet resuspended in 40 ul of deionized water. The clone DNAs are then electrophoresed along with whole pBR322 plasmid vector DNA to determine the relative molecular size of the DNA insert. Colonies which show DNA inserts of greater than 300 base pairs are chosen for the final colony screening procedure.

The final colony screening procedure is a screen for low copies of the clone within a total corn genome which, for the purpose of this analysis, is 30 copies or less. The average size of the selected clones is 1000 base pairs and the size of the corn genome is $4.5 \times 10^9$ base pairs. Dividing the latter into the former results in $2.22 \times 10^{-7}$, which is, on the average, the fraction of the corn genome which is represented by a clone of average desired size. Thus, if a clone were hybridized with lug of genomic corn DNA, those hybridization products showing a ratio of $2.22 \times 10^{-7}$ between genomic DNA and clone would roughly identify single copy clones.

To detect this ratio, a sandwich hybridizaton has been developed. One ug of denatured corn DNA is spotted onto a Genescreen® hybridization matrix along with spots containing 1, 10, 50, 250 picograms (pg) of pBR322 plasmid vector DNA and the spotted Genescreen® is baked at 95° C. for two to four hours. The DNA containing Genescreen® is then prehybridized for 6 to 16 hours in a hybridization solution containing 0.75M sodium chloride, 0.75M sodium citrate, 0.1% Ficoll, 0.1% Bovine Serum Albumin, 0.1% polyvinylpyrrolidone, 50 mM Tris pH 8.0, 0.5% SDS, 200 ug/ml Calf Thymus DNA, and 10% dextran sulfate. The DNA spots are then hybridized with approximately $1 \times 10^6$ cpms of labeled pBR322 and approximately 100 ng of cloned corn DNA in pBR322 vector. The unhybridized DNA is then washed off and an autoradiogram of the hybridization product is made. The clones which show a radioactive signal intensity in hybridization with the 1 ug genomic DNA spot which is equal to or less than the radioactive signal intensity of the 10 pg of the pBR322 hybridization product are clones which are considered to be single copy.

Clones which were selected as useful in Step 2 are radioactively labeled using random primers and reverse transcriptase as Step 3, labeling of the probes. Base denature the clone DNA and calf thymus (CT) random primers by adding 1 ul of 1N NaOH to 10 ul deionized water containing 1 ug of linear clone DNA and 50 ug of CT primers. Allow this to stand at room temperature for ten minutes and neutralize by adding 1 ul of 1.8M tris-HCl, 0.2M tris-base.

To 2 ul of the neutralized clone DNA and primer solution, add 2 ul of a solution containing 0.1M TrisHCl pH 8.3, 1.4M KCl, 0.1M $MgCl_2$ 0.02 M DTT, 1 ul each of 10 mM dXTPs, where X is A, G and T, 1.5 ul of 25 mM deoxycytidine triphosphate (dCTP); 5 ul of phosphorous 32 labeled dCTP, and 10 to 15 units of reverse transcriptase. Allow this mixture to stand at 37° C. for 30 to 45 minutes to label the clone DNA and then base denature and neutralize as above. The labeled clone is then separated from the unincorporated label by diluting the neutralized solution to 200 ul with a column buffer containing 10 mM tris-HCl pH 8.0, 2 mM EDTA, 50 mM NaCl and 0.5% SDS followed by chromatography on a G50 or G75 Sephadex® column in column buffer.

Practicing Step 4, preparation of plant DNA to be tested, genomic DNA from corn varieties C103, B57, B73, Mo17, Hy2, Wf9, and 3901 is prepared by removing and purifying the genomic DNA from the plant tissue. Plant tissue is then frozen in liquid nitrogen for five minutes and ground to a powder in a blender. To 10 g of this tissue powder, 100 mls of a solution which is 50 mM tris-HCl pH8, 10 mM EDTA, 1% SDS, 0.1M NaCl, and 10 mM betamecaptoethanol, is added and the suspension is ground in a polytron at low speed for twenty seconds. The solution is then heated to 65° C. for ten minutes to further break down the plant tissue and block any nucleases inherently present within the plant tissue. To this solution, is added 20 ml of 5M potassium acetate and it is placed in an ice bath for twenty minutes to precipitate undesirable matter. The precipitate is then centrifuged into a pellet and removed. To precipitate the genomic DNA from the supernant, the solution is brought to 35% isopropanol and chilled at −20° C. for thirty minutes. The precipitate is centrifuged into a pellet and lightly dried.

Further purification of the genomic DNA is accomplished through a second precipitation by dissolving the pellet in 5 ml of a solution containing 50 mM tris-HCl pH 8.0, and 10 mM EDTA; and then precipitating it with 1 ml of 5M ammonium acetate and 5 ml of isopropanol and centrifuging the precipitate into a pellet. The pellet is then washed in 80% ethanol, centrifuged and resuspended in 20 ml of TE. A final purification of the genomic DNA is accomplished by a cesium chloride gradient separation. To the 20 ml of TE containing the genomic DNA, 38.06 grams of cesium chloride are added and the volume brought to 40 ml with TE. The solution is centrifuged at 40,000 rpm at 20° C. for 20 hours. The resulting band of DNA is removed by suction with a 16 gauge needle, diluted three-fold with TE, brought to 50% isopropanol, and chilled to −20° C. for at least 2 hours. The resulting precipitate of pure genomic DNA is then centrifuged into a pellet which is resuspended in 1 ml of TE.

Thereafter, practicing Step 5, restriction of the test DNA, the genomic DNA is restricted with various restriction enzymes according to the manufacturer's specifications. The various restriction enzymes are initially chosen on the basis of two criteria. First, whether the enzyme will restrict the DNA of the plant variety being tested, and second, the cost of the restriction enzyme, particularly where exotic and expensive restriction enzymes may prove impractical for routine use. In corn, the restriction enzymes BamH1, BglII, EcoR1, HindIII, KpnI and SstI will form corn DNA fragments by cutting the DNA at a specific 6 base pair sequence; and the restriction enzymes HaeIII, HinfI, and TaqI will form corn DNA fragments by cutting the DNA at specific 4 and 5 base pair sequences. However, the restriction enzymes CfoI, HpaII, SmaI, and HhaI will not restrict corn DNA. The activity of restriction enzymes on a particular variety's DNA must be determined empirically.

In practicing Step 6, electrophoresis of the restriction fragments, the restriction fragments are separated on a neutral agarose gel by electrophoresis. The gel is formed by mixing 0.5% Seakem ME® agarose in a gel buffer which is 4.8% tris-base, 0.6% sodium acetate-3H$_2$O, 0.2% EDTA and is then brought to pH 8.0 with acetic acid. The solution is heated until the agarose is melted, is then cooled to 55° in a water bath, and the gel slabs cast. The restriction fragments are then loaded onto a gel slab by suspending them in a gel buffer containing 10% glycerol, 0.01% bromphenol blue and 0.5% SDS. The gel is then electrophoresed until the bromphenol blue has migrated three-fourths of the length of the gel, which is approximately obtained by applying 35 volts overnight or 75 volts for 6–8 hours to a gel slab 12 centimeters long.

In practicing Step 7, transfer of the electrophoresed DNA, the genomic DNA fragments are transferred to a suitable hybridization matrix by Southern Transfer. Genetran® or Genescreen® matrixes work equally well. The transfer is made using the transfer apparatus of FIG. 4, and the method previously described by denaturing the gel for 30 minutes in 0.2N NaOH and 0.6M NaCl; then neutralizing the gel for 30 minutes in 0.5M tris buffer pH 7.5, and 1.5M NaCl; and finally eluting the genomic DNA fragments from the gel onto the hybridization matrix with 25 mM sodium phosphate for 6 to 18 hours. The matrix is then washed for 15 minutes in a 0.3M sodium chloride and 0.3M sodium citrate solution and air dryed. Then the matrix is baked in a vacuum at 80° C. for 2–4 hours and washed in a solution containing 0.075M sodium chloride, 0.075M sodium citrate, and 0.1% SDS at 65° C. for 30 minutes. The dried matrix is then stored at 4° C. till needed.

In practicing Step 8, hybridization of restriction fragments with labeled probe, the genomic fragments are hybridized with the radioactive labeled clone prepared in Steps 1 through 3. The DNA fragment containing matrix is prehybridized in a sealed bag for at least four hours by submerging the matrix in a degassed buffer containing 0.075M sodium citrate, 0.75M sodium chloride, 0.1% bovine serum albumin, 0.1% polyvinylpyrrolidone; 0.1% ficoll, 50 mM tris pH 8.0, 0.5% SDS, 200 ng/ml calf thymus DNA, and 10% dextran sulfate. After prehybridization, the radioactively labeled clone is denatured by heating to 96° C. for 5 minutes and added to the matrix and buffer at a concentration of 200,000 counts per minute per ml. The genomic and cloned DNA fragments are then allowed to hybridize overnight at 65° C. The unhybridized DNA is removed by first washing the matrix three times for five minutes each, with a solution containing 0.03M sodium citrate, 0.3M sodium chloride and 0.1% SDS; and then washing it three times for twenty minutes each with a solution containing 0.0015M sodium citrate, 0.015M sodium chloride, and 0.2% SDS.

Step 9, detection of the hybridization product, is then accomplished by autoradiography. An autoradiogram is prepared by wrapping the hybridization matrix in Saran Wrap® to keep it from drying out and placing it against a sheet of x-ray film. To speed up exposure of the film, an image intensifier is placed on the opposite side of the film. After a few days, the X-ray film is developed to reveal the radioactive pattern on the matrix. This resulting autoradiogram will become part of the genomic "fingerprint" of the test plant.

Figure 7:
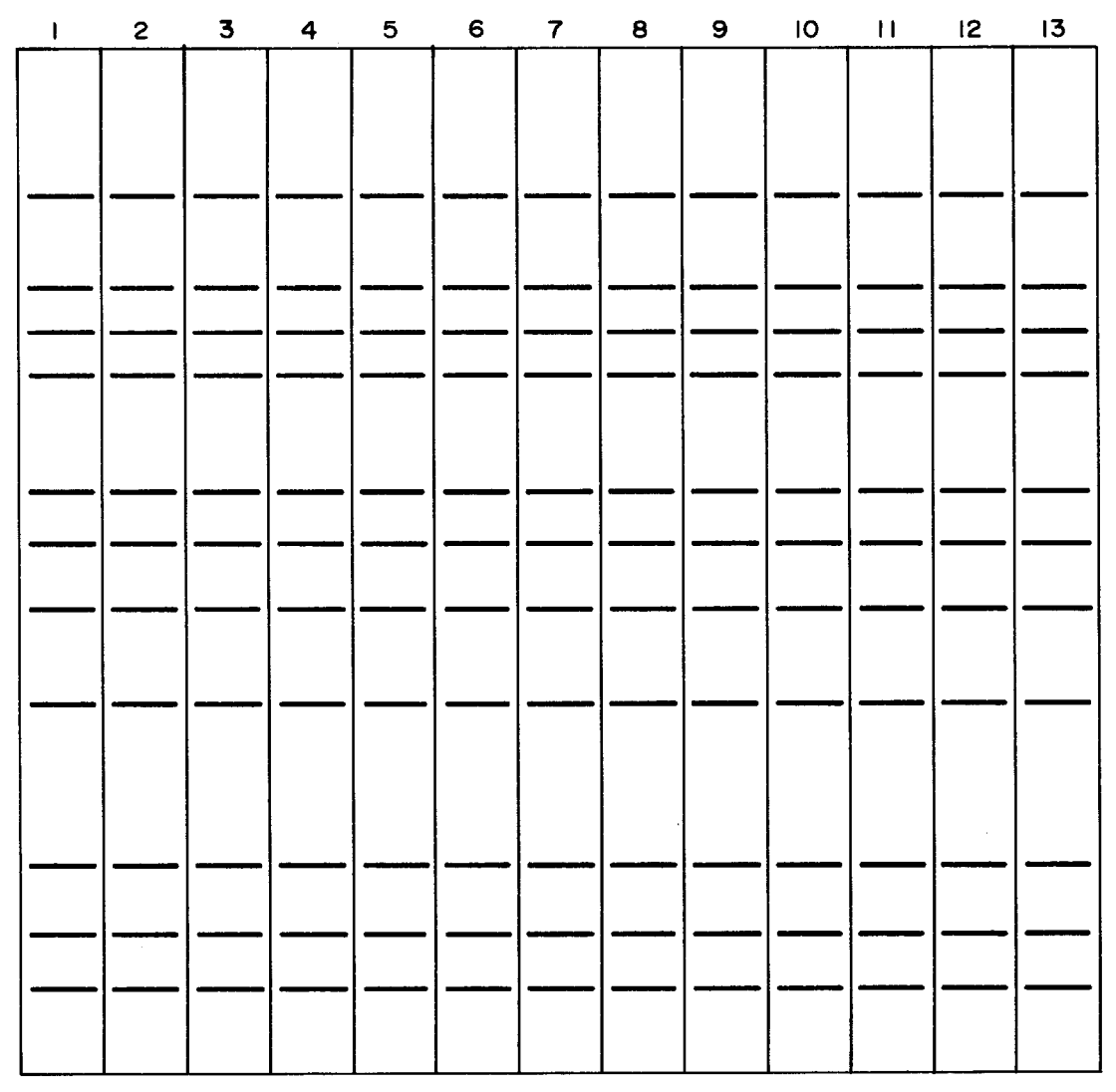
Figure 8:
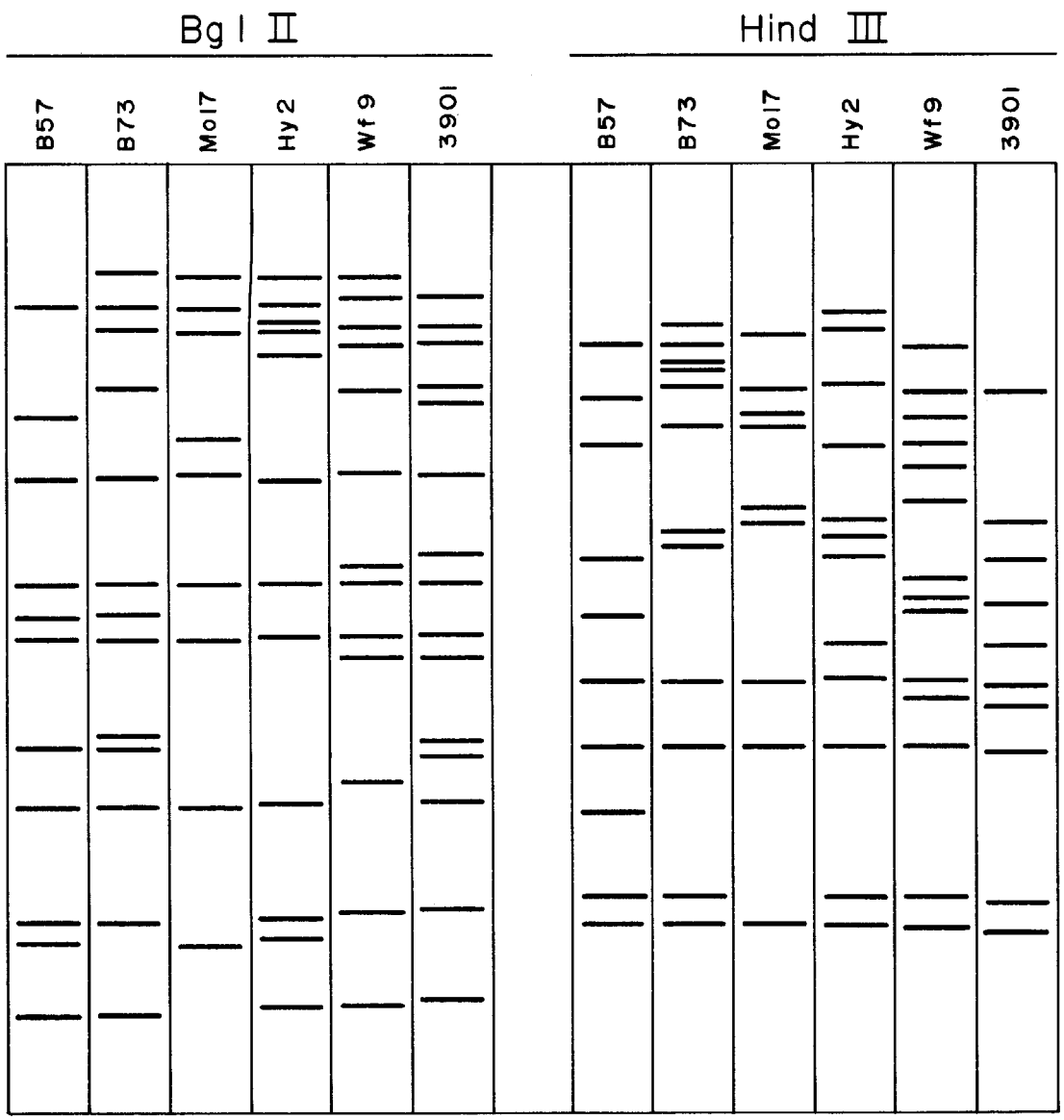
FIG. 8, a schematic representation of a resulting autoradiogram of six corn varieties restricted with two different enzymes.

FIGS. 7 and 8 represent autoradiograms produced in practicing Step 8 as they apply to Steps 9 and 10. In FIG. 7, thirteen individual C103 plants were processed through to purified DNA, the DNAs restricted with BglII, electrophoresed on a 0.7% agarose gel, blotted, and hybridized with a low copy number probe. No differences were detected in any of the individual plants when examining eleven different fragments. The autoradiogram represented in FIG. 7 illustrates that individual plant identity can be determined and that variation between individual plants within a variety is fairly low. To establish a unique proof of identity, Steps 1 through 7 are repeated a number of times with different probes and enzymes to establish a unique "fingerprint" by examining a few hundred different fragments at different genomic locations.

FIG. 8 represents an autoradiogram which illustrates the types of dissimilarity observed when testing genetically different varieties. DNA, from the different varieties B57, B73, Mo17, Hy2, Wf9, and 3901, was digested with Bgl II and Hind III, electrophoresed, blotted, and hybridized with the same probe used in FIG. 7.

In a practice of Step 11, B57 can be distinguished from B73 because of the 21 B57 bands represented in FIG. 8 and the 25 B73 bands, only 14 are the same, i.e., have the same mobility by electrophoresis. Any variety which shows the same bands as B57 would be determined to be identical to B57. By using more restriction enzymes and thus generating more bands, one could increase the reliability of determining the relatedness between any two varieties.

It can, therefore, be clearly seen that, while some bands are shared in common between varieties, many vary quite a bit such that each variety can be clearly distinuished from any other. The banding patterns are quite different for the same variety and probe when a different restriction enzyme is used, as would be expected. By examining several more combinations of probes and restriction enzymes, a pattern of many different fragments can be assembled such that the genetic relatedness of isolates and varieties can be determined. From these two figures, the two requirements for this system are demonstrated: low variance of individual plants within a variety and high variance between varieties.

Whereas this invention is here illustrated and described with specific reference to an embodiment thereof presently contemplated as the best mode of carrying out the invention in actual practice, it should be understood that various changes may be made in adapting the invention to different plant varieties without departing from the broader inventive concepts disclosed herein and comprehended by the claims that follow.

What is claimed is:

1. A process for comparing plants comprising the steps of:
   (A) providing a plurality of labelled DNA probes, wherein each probe of said plurality consists of a base sequence represented in low copy number in the genome of a first plant;
   (B) under hybridization conditions, bringing each of said DNA probes into contact with restriction fragments of genomic DNA of said first plant which are arrayed on a nucleic acid molecular hybridization matrix in a size-dependent manner, thereby to produce a plurality of nucleic acid molecular hybridization products;
   (C) from said plurality of nucleic acid molecular hybridization products, ascertaining a first pattern of hybridization of said DNA probes to said restriction fragments
   (D) repeating steps (B) and (C) with restriction fragments of the genomic DNA of a second plant, said restriction fragments of the genomic DNA of said second plant generated in the same way as said restriction fragments of the genomic DNA of said first plant, thereby ascertaining a second pattern of hybridization of said DNA probes to said restriction fragments of from said second plant; and
   (E) comparing said first pattern of hybridization to said second pattern of hybridization.

2. A process according to claim 1, wherein step (B) comprises bringing said DNA probes into contact with restriction fragments of genomic DNA of said first plant, said genomic DNA having been separated on a neutral agarose gel by electrophoresis and then transferred to said nucleic acid molecular hybridization matrix via a Southern transfer.

3. A process according to claim 1, wherein each of steps (C) and (D) comprises subjecting said nucleic acid molecular hybridization products, respectively, to autoradiography to ascertain said first and second patterns of nucleic acid molecular hybridization.

4. A process according to claim 1, wherein step (B) comprises bringing said DNA probes into contact with 300 to 500 restriction fragments.

5. A process according to claim 1, wherein said first plant and said second plant are corn plants.

* * * * *